`US008529915B2`

United States Patent
Wei

(10) Patent No.: US 8,529,915 B2
(45) Date of Patent: Sep. 10, 2013

(54) (R)-(-)-1,2-PROPANEDIOL COMPOSITIONS AND METHODS

(76) Inventor: Edward T. Wei, Berkeley, CA (US)

( * ) Notice: Subject to any disclaimer, the term of this patent is extended or adjusted under 35 U.S.C. 154(b) by 0 days.

(21) Appl. No.: 13/065,185

(22) Filed: Mar. 16, 2011

(65) Prior Publication Data
US 2012/0053152 A1     Mar. 1, 2012

Related U.S. Application Data

(60) Provisional application No. 61/340,766, filed on Mar. 20, 2010.

(51) Int. Cl.
*A61K 31/045*     (2006.01)
(52) U.S. Cl.
USPC .............................. 424/400; 514/75; 514/738
(58) Field of Classification Search
USPC ................................. 424/400; 514/75, 738
See application file for complete search history.

(56) References Cited

U.S. PATENT DOCUMENTS

| 4,070,496 A | * | 1/1978 | Rowsell et al. .................. 424/45 |
| 2008/0227857 A1 | | 9/2008 | Wei | |

FOREIGN PATENT DOCUMENTS

| GB | 2 451 503 A | 2/2009 |
| WO | WO 2004/037764 A1 | 5/2004 |

OTHER PUBLICATIONS

Rowe et al., Handbook of Pharmaceutical Excipients, Propylene Glycol, Pharmaceutical Press, 5$^{th}$ Edition, 2006, 624-626.*
Chemical-Supermarket.com, Propylene Glycol, printed from http://www.chemical-supermarket.com/product.php?productid=73, Sep. 22, 2012, 2 pages.*

* cited by examiner

*Primary Examiner* — Gigi Huang

(57) ABSTRACT

Short-chain 2- to 3-carbon alcohols are used as solvents for cooling agents in the preparation of topical therapeutic and cosmetic formulations. Some of these alcohols, especially ethanol, inhibit the ability of the cooling agent to activate its target receptor. In one embodiment of this invention, (R)-1, 2-propanediol is used as an alcoholic solvent for the topical delivery of cooling agents to biological surfaces. This propanediol enantiomer has a minimum inhibitory effect on cooling with respect to standard 2- to 3-carbon alcoholic solvents, and functions to substantially protect the agent's cooling activity from inhibition when in the presence of a short-chain alcohol.

1 Claim, 2 Drawing Sheets

Effects of cooling agent CPS-369, 10 mg/ml, in ethanol (diamonds), 1,3-propanediol (squares), (S)-1,2-propanediol (triangles) and (R)-1,2-propanediol (circles).

Fig. 1. Effects of cooling agent CPS-369, 10 mg/ml, in ethanol (diamonds), 1,3-propanediol (squares), (S)-1,2-propanediol (triangles) and (R)-1,2-propanediol (circles).
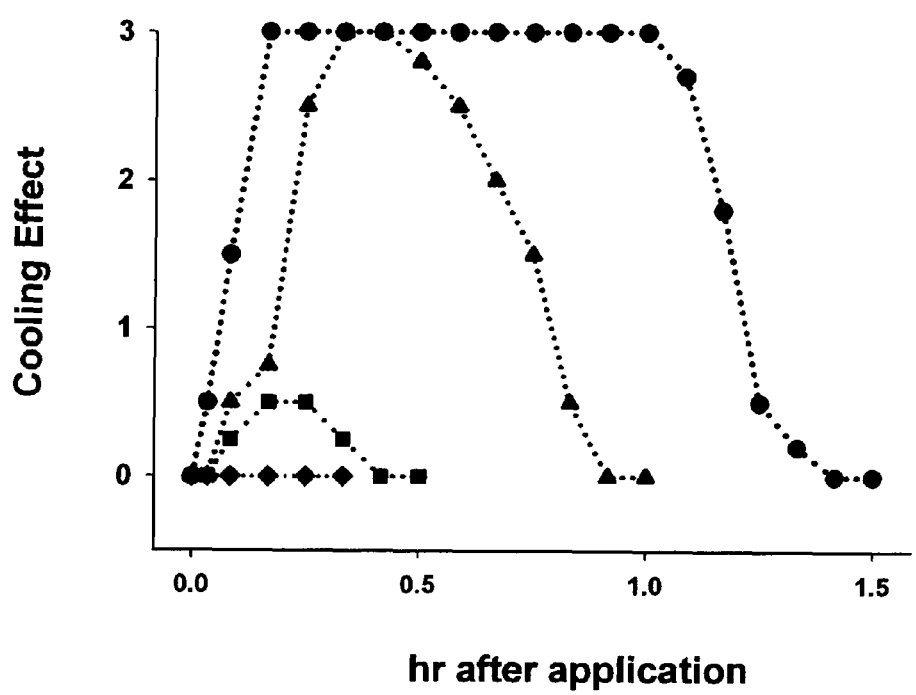

Fig. 2. Effects of cooling agent WS-5, 10 mg/ml, in ethanol containing (vol/vol) 0% (diamonds), 10% (squares), 20% (triangles), or 40% (circles) of (R)-1,2-propanediol.
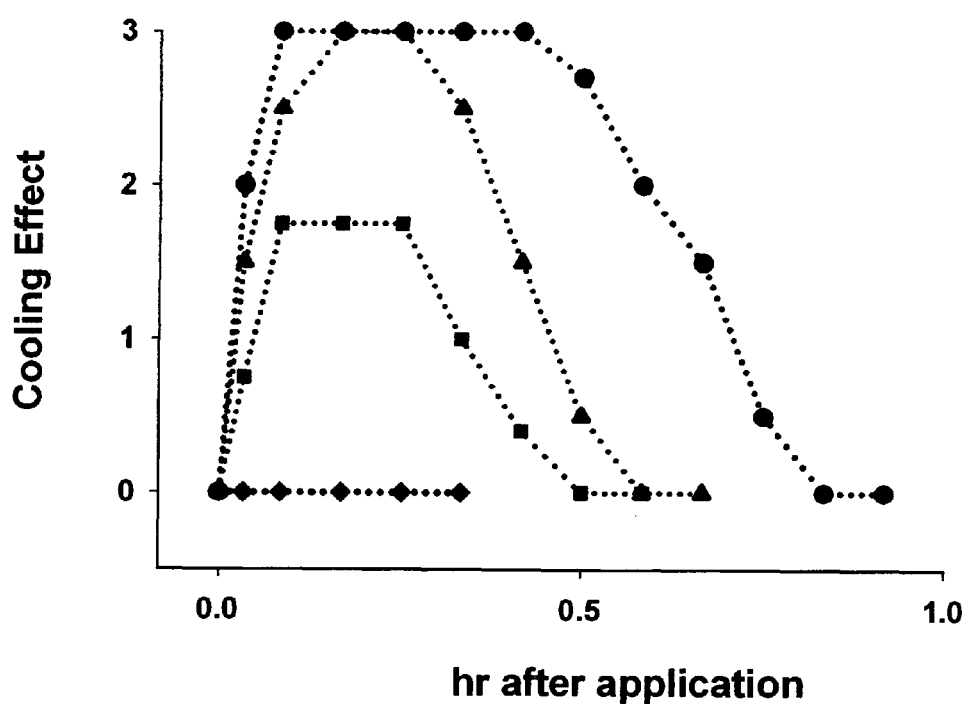

(R)-(-)-1,2-PROPANEDIOL COMPOSITIONS AND METHODS

RELATED APPLICATION

This application is related to:
U.S. Provisional Application No. 61/340,766 filed 20 Mar. 2010
the contents of which are incorporated herein by reference in their entirety.

BACKGROUND OF THE INVENTION

1. Field of the Invention

This discovery generally relates to solvents or vehicles for compounds that target sensory elements on nerve fibers, which are usefully administered to refresh and to cool the skin and mucous membranes.

2. Description of the Related Art

About three decades ago, a group of scientists synthesized over 1200 compounds in an attempt to find cooling agents that had properties better than menthol. Their results were summarized in a paper (Watson et al. New compounds with the menthol cooling effect. J. Soc. Cosmet. Chem. 29, 185-200, 1978.). From this research, an N-alkyl-cycloalkyl- and an N-alkyl-alkyl carboxamide, WS-3 (2-Isopropyl-5-methyl-cyclohexanecarboxylic acid ethylamide), WS-5 ([(2-Isopropyl-5-methyl-cyclohexanecarbonyl)-amino]-acetic acid ethyl ester), and WS-23 (2-Isopropyl-2,3,N-trimethyl-butyramide), respectively, reached the market and are used as additives to confectionery, comestibles (e.g., candy, chewing gum), and toiletries. Other menthol-like cooling compounds in commercial use for applications to skin and mucous membranes are, for example, menthyl lactate (Frescolat ML), menthoxypropanediol (Cooling Agent 10), and 2-isopropyl-5-methylcyclohexyl 4-(dimethylamino)-4-oxobutanoate. The recent information on cooling agents used for topical applications has been reviewed (see, e.g., Erman, M. B. "Cooling agents and skin care applications", Cosmetics & Toiletries, 120, 105-118, 2005; Erman, M. B. "Progress in physiological cooling agents", Perfumer & Flavorist, 29, 34-50, 2004; Jacobs, P. and Johncock, W., "Some like it cool", Parfumerie and Ksometik, 80, 26-31, 1999).

Cooling compounds are described in U.S. Pat. No. 6,919,348 (Wei et al., Jul. 19, 2005). Other molecules investigated by Wei are described in: US 2005/0059639, published Mar. 17, 2005, Ophthalmic Compositions and Methods for Treating Eye Discomfort and Pain; US 2005/0159394, published Jul. 21, 2005, Aryl-Substituted Derivatives of Cycloalkyl and Branched Chain Alkyl Carboxamides and Carboxylic Acids Useful as Antinociceptive Drugs For Peripheral Targets; US 2005/0187211, published Aug. 25, 2005, N-Aryl$_s$-Carboxamide Compositions and Methods; and WO 2006/103401, N-Alkylcarbonyl-Amino Acid Ester and N-Alkylcarbonyl-Amino Lactone Compounds and Their Use, published Oct. 5, 2006.

In the delivery of these cooling agents to the desired biological targets, formulations for the skin (e.g. lotions, creams, ointments) and formulations for the respiratory tree or oral cavity (e.g. vapors, sprays) that are liquid, semi-liquid, or non-particulate, require a solvent for the active cooling ingredient. Frequently, two or three carbon alcohols such as ethanol, isopropyl alcohol, and racemic 1,2-propanediol, are used.

Weil et al. 2005 [Molecular Pharmacology 68: 518-527, 2005] reported that 0.5% ethanol in the medium inhibited the TRP-M8 receptor response to (-)-menthol by 50%, and the response is almost totally lost at 3% concentration of ethanol. The TRP-M8 receptor is the putative target on neurons that mediate cooling and anti-irritant sensations. Benedikt et al. 2007 [J. Neurochemistry 100: 211-224, 2007], confirmed Weil's results and noted that the activity for in vitro inhibition was methanol<ethanol<isopropanol<butanol. Dimethylsulfoxide, a solvent with a dielectric constant similar to water, was claimed to be less inhibitory. Benedikt et al. discussed the possible mechanisms of ethanol interference with receptor activity and suggested: 1) low molecular weight alcohols are absorbed into lipid bilayers, and may seriously affect the mechanical properties of cell membranes and/or 2) affect secondary intracellular messengers such as phosphatidylinositol-4,5-biphosphate that transduce the receptor activation to neuronal signals. These studies by Weil et al. and by Benedidkt et al. showed that the solvent medium is important for the bioactivity of cooling agents.

Ideally, a solvent should dissolve the cooling agent and deliver the active ingredient to target without interfering with bioactivity. Chemicals such as 1,2-ethanediol, methanol, dimethylsulfoxide, and butanols are not used in topical formulations because of potential hazards. Thus, the choice of an ideal solvent among the two and three carbon alcohols is limited.

The short-chain alcohols are generally thought to interact with biological membranes by non-specific physical forces such as interfacial tension, mechanical compressibility per area/molecule, and affecting the permeability parameters of fluid lipid bilayers (Ly and Longo, Biophysical J. Biophys. J. 87: 1013-1033; 2004). Harris et al. (Ethanol's molecular targets. Science Signaling, Jul. 15, 2008), recently summarized evidence for an alternative view, namely, that ethanol acts on specific "pockets" on protein receptor surfaces to modulate function.

SUMMARY OF THE INVENTION

It has been found that while solvents such as ethanol, n-propanol, isopropanol, 1,3-propanediol, 1,3-butanediol, and (S)-propane-1,2-diol inhibit the actions of cooling agents, surprisingly, (R)-propane-1,2-diol, relative to these other solvents, is substantially devoid of inhibitory action and will facilitate and prolong cooling. This phenomenon is dramatic and unexpected. Thus, (R)-propane-1,2-diol is an ideal solvent for cooling agents applied to a biological surfaces such as skin and mucous membranes.

In one aspect of the present invention, an adjuvant useful for topical cooling when combined with therapeutic or cosmetic formulations, is provided that comprises a cooling agent, the agent providing cooling activity unless inhibited by the presence of a short-chain alcohol; and, a quantity of (R)-1,2-propanediol in which the cooling agent is dissolved, the quantity of (R)-1,2-propanediol being sufficient to substantially protect the cooling agent's cooling activity from inhibition when in the presence of a short-chain alcohol.

The specific structure of (R)-1,2-propanediol is shown in Formula 1, below.

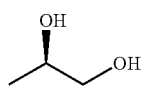

(R)-Propane-1,2-diol

Formula 1. (R)-1,2-propanediol [(R)-(−)-1,2-propanediol] [CAS No. 4254-14-2], is a colorless, viscous liquid, with a density of 1.036 g/ml.

The (R)-1,2-propanediol may be used to facilitate delivery of cooling agents onto the surfaces of the skin, oral cavity, and upper respiratory tract without interference with the pharmacological activity of the cooling agents on the sensory target. Compositions according to the discovery, formulated, with (R)-1,2-propanediol and a cooling agent, may also be used to inhibit the perception of itch, pain, and irritation from the body's surfaces. Topical uses on skin may also be used to alter the activity of keratinocytes and melanocytes (cells that respond to cooling agents which activate Trp channels).

In another aspect of the present invention, a method for improving cooling agent activity in a liquid or semi-liquid therapeutic or cosmetic composition for topical application is provided comprising the steps: providing a cooling agent requiring a solvent, with cooling activity unless inhibited by the presence of a short-chain alcohol; and, dissolving the cooling agent in a 1,2-propanediol solvent that is enantiomer-enriched with respect to (R)-1,2-propanediol, whereby the (R)-1,2-propanediol in which the cooling agent is dissolved is sufficient to substantially protect the agent's cooling activity from inhibition when in the presence of a short-chain alcohol.

Other aspects, advantages, and applications of this invention will become apparent upon reading the specification and the appended claims.

BRIEF DESCRIPTION OF THE DRAWINGS

In FIG. 1 the duration of cooling (hours) for CPS-369 dissolved 10 mg/ml in four different solvents is graphically illustrated. The first solvent was ethanol (diamonds), the second 1,3-propanediol (squares), the third (S)-1,2-propanediol (triangles) and the fourth (R)-1,2-propanediol (circles). Each test solution was applied with a cotton-tipped stick onto the philtrum skin and the cooling effect recorded.

In FIG. 2 the cooling effects of WS-5, 10 mg/ml, applied to the philtrum skin, is graphically illustrated. WS-5 was dissolved in an ethanolic solution containing volume/volume either 0% (diamonds), 10% (squares), 20% (triangles), or 40% (circles) of (R)-1,2-propanediol.

DETAILED DESCRIPTION OF THE INVENTION

Pharmacology of Cooling Agents

Cooling of the skin and mucous membranes is detected by a subset of primary sensory afferents that have receptors on nerve endings. These sensory fibers exhibit a rhythmic, ongoing discharge at neutral temperatures that increases in response to skin temperature reductions (from 33° C. to 23° C.) and is suppressed by warming. The dynamic information is propagated along axons in spike trains, at about 20 to 40 impulses/sec, to central neurons, leading in humans to cooling sensations. This type of sensation is mimicked, for example, by facial skin exposure to ambient temperatures of 15° C. to 22° C.

The multiple actions of (−)-menthol and related cooling agents on sensory processes are utilized in compositions for foods, confectionery, flavors, chewing gum, mouth fresheners, liptsticks, and other comestibles (items put in the mouth), beverages, tobacco products, toiletries, over-the-counter pharmaceutical compositions for nasal and airway symptoms, for gastrointestinal tract distress, for inhibiting melanocyte activity, and as a counter-irritant for alleviating discomforts of skin and muscle. Menthol confectionery also has alerting effects on the central nervous system and may suppress appetite. If the delivery medium is liquid or partially liquid, it is desirable to have a solvent for the cooling agent that will not interfere with bioactivity.

Preferred cooling agents for practicing this invention target the TRP-M8 receptor and can be topically delivered in liquid or partially liquid form. Suitable cooling agents include (−)-menthol, p-menthyl lactate, the N-substituted p-menthane carboxamides such as WS-3, WS-5 and WS-23, and the trialkylphosphine oxides such as CPS-147 (1-(Di-sec-butyl-phosphinoyl)-hexane) and CPS-148 (1-(Di-sec-butyl-phosphinoyl)-heptane). Also included are CPS-369 [(R)-2-[((1R,2S,5R)-2-isopropyl-5-methyl-cyclohexanecarbonyl)-amino]-propionic acid ethyl ester], CPS-410 [(R)-2-[((1R,2S,5R)-2-isopropyl-5-methyl-cyclohexanecarbonyl)-amino]-propionic acid n-propyl ester], and CPS-412 [(R)-2-[((1R,2S,5R)-2-isopropyl-5-methyl-cyclohexanecarbonyl)-amino]-propionic acid n-butyl ester]

Bioassays of Cooling Actions in Various Solvents

Psychic events such as cooling, refreshment, relief of irritation, itch, and pain, cannot be directly expressed by animals. Receptor assays, based on cells transfected with the genes for proteins associated with thermosensation (e.g., TRP-M8 or TRP-A1) may be used as a substitute model of sensory processes. The receptor assays yield quantitative data, but these assays give no information on onset and offset of action, or on the quality of human sensations evoked by the chemicals. Thus, the best information on the pharmacological properties of chemicals is derived from direct tests on humans.

Rowsell et al. (U.S. Pat. No. 4,178,459) tested the properties of N-substituted p-menthane carboxamides on volunteers by putting filter paper (1×1 cm), impregnated with a known amount of compound, onto the dorsal surface of the tongue of the test subject. After 30 seconds, the subject was required to report presence or absence of a cooling effect. These data were reported as "Threshold, μg" and refer to the threshold amount of the test substance that produces cooling sensations upon application onto the tongue of a panel of human volunteers. The average threshold of (−)-menthol for 6 subjects was 0.25 μg, but there was a 100-fold variation in individual sensitivity. Ethanol was frequently used as a solvent in these studies on menthol-like cooling agents and may have contributed to the variation in individual sensitivity, as we now know that ethanol as the primary solvent interferes with the detection of cooling sensations.

It has been found that the cooling and sensory properties of a chemical in various solvents can be tested by dissolving a test substance in an alcoholic solvent and singly applying 0.10 to 0.20 ml of the solution onto the skin surface using a cotton-tipped applicator (e.g. Q-tips®). The term "alcoholic solvent" refers to a chemical with one to four carbons with at least one hydroxyl group attached to a carbon atom. A reliable place for topical application is the skin above the upper lip (above the vermilion border of the lips), on the philtrum, lateral to the philtrum until the nasolabial folds, and on the lower nostrils (subnasale). This part of the face is known to be densely innervated with cold receptors, second only to the surfaces of the eyeball and anogenitalia. Tingling, cool and cold sensations from the skin may be experienced and rated for time of onset and intensity.

The intensity of the subjective skin sensation is rated as 0, 1, 2 or 3 with 0 as no change, 1 as slight coolness, cold, or tingling, 2 as clear-cut signal of coolness, cold, or tingling, and 3 as robust cooling or cold. The intervals for recording sensations are 5 to 10 minutes, until two successive zeroes are obtained. The results (shown in the Figures) are averaged values of 4 to 6 separate trials in the same individual. The data are plotted using SigmaPlot (Systat Software, Point Richmond Calif.) and a smoothing function with a negative exponential was used for analysis and statistical fit of the results. The onset of drug action is taken as the time to reach 2 units of coolness intensity, and offset of drug action is the time when coolness intensity drops below 2, after previously surpassing 2 units. The duration of cooling action is defined as the offset time minus the onset time and the primary index of effect. As described in Examples, the test compounds were tested at 2 to 10 mg/ml of vehicle.

Surprisingly and unexpectedly, only (R)-1,2-propanediol, by contrast to the standard two or three carbon alcoholic solvents (see Table 1), did not interfere with the cooling actions of various cooling agents. Without wishing to be bound by theory it is hypothesized that this effect may be related to the stereospecific (R)- or dextrorotatory configuration of the second carbon in propanediols. Thus, this preferred solvent embodiment can be used to optimize cooling agent activity when such agents are delivered to skin and mucous membranes.

Stereoisomers are compounds which have the same molecular formula but differ in the arrangement of their atoms in space. Enantiomers are pairs of stereoisomers which are nonsuperimposable mirror images; they possess identical physical and chemical properties within an achiral environment. Enantiomers are distinguished in the presence of polarized light. The two molecules in a pair of enantiomers rotate a plane of polarized light with equal intensities, but in opposite directions. The dextrorotatory isomer (+ or d) rotates the plane of polarized light clockwise; the levorotatory isomer (− or l) rotates the plane of polarized light counterclockwise. An equal mixture of (+) and (−)-enantiomers is a racemic mixture or racemic compound and does not rotate a plane of polarized light. Thus, a non-racemic mixture is one wherein one enantiomer is greater than 50%. Increasing the concentration of one enantiomer gives an "enantiomer-enriched" mixture.

(R)-1,2-propanediol is a relatively safe molecule for human use because the racemate is already accepted as a solvent for cosmetics and pharmaceuticals (Lakind et al. A review of the comparative mammalian toxicity of ethylene glycol and propylene glycol. Critical Reviews in Toxciology 29: 331-365, 1999). In rodents, the median lethal dose of racemic 1,2-propanediol is about 25 ml/kg of body weight, indicating large doses can be administered orally without immediate danger. An estimated "safe" dose for humans, based on intravenous infusion studies of racemic 1,2-propanediol, is 1 g per kg body weight per day (Wilson et al. Chest 128: 1674-1681, 2005). Furthermore, the metabolic pathways of the two enantiomers of 1,2-propanediol generate L- and D-lactic acids which are then converted to pyruvate and then acetic acid by natural endogenous mammalian enzymes (Ewaschuk et al. J. Nutrition 135: 1619-1625, 2005).

Topical Uses of (R)-1,2-Propanediol as a Solvent

In one aspect of this discovery, a cooling embodiment is topically applied with (R)-1,2-propanediol as the solvent. In this non-racemic solvent, the preponderant or major species is the (R)-isomer. By "topically" is meant application onto surfaces of the body in contact with air, which includes the skin, the ocular surfaces, the lips, the upper (nasal membranes and pharyngeal surfaces) and lower respiratory tracts, and the lumen of the gastrointestinal tract. Particularly favored sites of application are the surfaces innervated by the trigeminal and glossopharyngeal nerves which include the facial skin, eyes, lips, nasal and oral cavities and the throat. Another favored site is the surfaces of the elbow and knee which are frequently associated with the pruritus of atopic eczema and psoriasis. And yet another favored site is the scalp which can be a site of inflammation in psoriasis and contact dermatitis.

Therapeutic uses for such topical formulations are contemplated in a lotion, cream, ointment, in aerosolized formulations, in wipes, or in oral liquid formulations and include utility for a) alleviation of irritation, itch and pain from various forms of dermatitis (atopic, contact and irritant); b) pain from burned, traumatized, diseased, anoxic, or irritated skin (e.g., skin damaged by laser surgery, diabetic ulcers, sunburn, radiation), and from procedures related to wound debridement; c) itch and discomfort from skin infections, insect bites, sunburn, photodynamic treatment of skin (e.g., actinic keratoses, basal cell carcinoma); d) pruritus due to xerosis, frequently seen in the elderly, or psoriasis; e) mucositis, stomatitis, cheilitis or itching of the lips from cold sores and gingivitis; f) pruritus ani, hemorrhoidal discomfort, pain from anal fissures, pain or itch from anal fistulas, pain from hemorrhoidectomy, perineal inflammation, anogenital skin inflammation and discomfort due to various local causes such as incontinence, diaper rashes, perineal inflammation; g) vulval pruritus and pain (e.g., from candidiasis or idiopathic, such as vulva vestibulitis and vulvodynia), dyspareunia, anogenital infections, including warts and sexually transmitted diseases, viral infections of the skin (especially in immunocompromised patients); and h) nostril and nasal or upper airway discomfort from breathing obstruction, e.g., congestion, rhinitis, asthma, bronchitis, emphysema and chronic obstructive pulmonary diseases, dyspnea, sleep apnea and snoring.

As sensory processes are also important in hollow viscus, these embodiments may be delivered nasally, or inhaled or encapsulated for oral delivery to the surfaces of the gastrointestinal tract and the airways. For the lower gastrointestinal tract, such formulations may be used to relieve heartburn, peptic pain, and the discomforts of the irritable bowel syndrome and of inflammatory bowel diseases. The preferred method of liquid delivery would be enteric-coated capsules. Alternatively, the formulation may be extruded onto the gut surface using a controlled release device such as an osmotic mini-pump. For the upper airways, the liquid or aersolized formulation may be inhaled or delivered as a mist or spray.

Suitable topical formulations, for example, include compositions such as liquids, aerosols, lotions, liniments, creams and ointments, and cosmetic preparations. A wide variety of vehicles will be suitable, depending upon the particular product involved, such vehicles including liquids, emulsions, foams and gels. Examples of skin products include acne treatment preparations containing benzoylperoxide. Examples of mouth spray delivery systems are currently marketed products such as Listerine Pocket Mist™ (Pfizer Consumer Healthcare) and Sweet Breath-breath spray (HealthTech., Inc.). Examples of aerosol/nebulizer delivery systems are those systems marketed by Omron Healthcare, Inc., and A.D.A.M., Inc. For delivery onto the skin, (R)-1,2-propanediol may be considered for use, for example, in a wipe, as the primary solvent instead of racemic propanediol which is frequently found together with water in commercial cleansing products (e.g. Cottony Cloths, Supreme and Soft Cloths, Supreme, from CVS Pharmacy).

EXAMPLES

Example 1

(R)-1,2-propanediol, (S)-1,2-propanediol, 1,3-propanediol, and racemic 1,3-butanediol were purchased from Sigma-Aldrich Co. Ethanol, n-propanol, isopropyl alcohol and racemic 1,2-propanediol were obtained from local sources. The cooling agents selected for testing were (−)- menthol, WS-3, WS-5 [((1R,2S,5R)-2-isopropyl-5-methyl-cyclohexanecarbonyl)-amino]-acetic acid ethyl ester], CPS-147, CPS-148, CPS-368 [(R)-2-[((1R,2S,5R)-2-isopropyl-5-methyl-cyclohexanecarbonyl)-amino]-propionic acid methyl ester], CPS-369 [(R)-2-[((1R,2S,5R)-2-isopropyl-5-methyl-cyclohexanecarbonyl)-amino]-propionic acid ethyl ester], CPS-410 [(R)-2-[((1R,2S,5R)-2-isopropyl-5-methyl-cyclohexanecarbonyl)-amino]-propionic acid n-propyl ester] and CPS-412 [(R)-2-[((1R,2S,5R)-2-isopropyl-5-methyl-cyclohexanecarbonyl)-amino]-propionic acid n-butyl ester]. These compounds and their methods of synthesis are described in US 2008/0227857 A1 (Sep. 18, 2008) and in M. Bödding et al. Characterisation of TRPM8 as a pharmacophore receptor. Cell Calcium. 2007 vol. 42: 618-28, incorporated herein by reference.

For assays on the skin, the cooling agent(s) was dissolved in the alcoholic solvent to yield a 2, 2.5, 3, 5 or 10 mg/ml solution. Using a cotton-tipped applicator (e.g. Q-tips®) 0.10 to 0.25 ml of the test solution was applied to the skin above the upper lip, on the philtrum, and lateral to the philtrum up to the nasolabial folds, and the onset and duration of cooling sensations noted. The intensity of the subjective skin sensation was rated as 0, 1, 2 or 3 with 0 as no change, 1 as slight coolness, cold, or tingling, 2 as clear cut signal of coolness, cold, or tingling, and 3 as robust cooling or cold. The interval for recording sensations was at 5 to 10 minute intervals, until at least two successive zeroes were obtained. The results were averaged values of 3 to 6 separate trials in the same individual. The "onset" is the time taken to reach a coolness intensity value of 2. If the tested solution did not reach a value of 2 then it was considered to be inactive. The "off-set" is when the coolness intensity drops below 2, and the duration is the time of off-set minus the time of onset. The area under the curve (AUC) also gives an estimate of the intensity and duration of drug action and can be obtained from the plotted data using SigmaPlot (Systat Software, Point Richmond Calif.). The AUC is given in average ±S.E.M. units which is the product of cooling intensity×min. Thus, if an AUC value of 180 is obtained, that means the cooling intensity of 3 was accumulated for at least 60 min, even though the overall duration of the effect would be longer, e.g. 75 min, because of the time taken for the onset and off-set of coolness.

The test results for CPS-369, a potent cooling substance, are shown in FIG. 1 and Table group (ethanol, n-propanol and isopropanol) resulted in loss of cooling activity. Dissolution of CPS-369 in the dihydroxyalcohols, 1,3-propanediol and racemic 1,3-butanediol also resulted in significant loss of cooling activity. Among the 1,2-propanediols, the (R)-1,2-propanediol enantiomer was the best solvent for retaining the cooling action of CPS-369. Based on AUC, the (S)-1,2-propanediol enantiomer solution had only 47% of the activity of the (R)-1,2-propanediol enantiomer.

TABLE 1

Cooling activity of CPS-369 at 10 mg/ml in different alcoholic solvents.

| Solvent | Cooling Activity % (relative to (R)-1,2-propanediol) |
| --- | --- |
| (R)-1,2-propanediol | 100 |
| (S)-1,2-propanediol | 47 |
| racemic 1,3-butanediol | 10 |
| 1,3-propanediol | inactive |
| ethanol | inactive |

TABLE 1-continued

Cooling activity of CPS-369 at 10 mg/ml in different alcoholic solvents.

| Solvent | Cooling Activity % (relative to (R)-1,2-propanediol) |
| --- | --- |
| n-propanol | inactive |
| isopropanol | inactive |

The test solution was applied to the philtrum skin and cooling sensations recorded. If coolness intensity did not exceed 2 units of coolness (as defined in the philtrum bioassay procedure) at any time after application, the solution was considered "inactive".

Example 2

Racemic 1,2-propanediol (propylene glycol) is a standard solvent for many cosmetic and dermatological formulations. The activities of cooling agents in racemic 1,2-propanediol vs (R)-1,2-propanediol were compared and the results shown in Table 2. It can be seen that the (R)-enantiomer is a solvent that provides more cooling activity than the racemate. For six of the seven compounds testing, the cooling activity measured in AUC units was about two times greater in (R)-1,2-propanediol than in racemic 1,2-propanediol. The favorable properties of (R)-1,2-propanediol as a solvent were unexpected, surprising, and have practical utility. For example, a smaller amount, e.g. 50% less, of cooling agent would be required to achieve the same effect. Also, in situations where it is desirable to decrease the amount of the 1,2-propanediol solvent in the formulation, use of (R)-1,2-propanediol can decrease the required amount by about 50%.

TABLE 2

Comparison of cooling activity of various agents in racemic 1,2-propanediol versus (R)-1,2-propanediol.

| Test Substance and test concentration | racemic-1,2-propanediol | (R)-1,2-propanediol (Inventive Embodiment) | % Ethanol in mixture vol/vol |
| --- | --- | --- | --- |
| CPS-369, 5 mg/ml | 134 ± 16 | 218 ± 12* | 1 |
| CPS-410, 5 mg/ml | 122 ± 12 | 281 ± 7* | 1 |
| CPS-412, 5 mg/ml | 127 ± 10 | 243 ± 5* | 1 |
| WS-3, 20 mg/ml | 64 ± 6 | 122 ± 8* | 3 |
| CPS-147, 3 mg/ml | 64 ± 4 | 81 ± 4* | 2 |
| CPS-148, 2 mg/ml | 75 ± 6 | 173 ± 15* | 1 |

Use of (R)-1,2-propanediol Is a preferred embodiment of the invention. The measurement of drug action are in units of AUC (area-under-the curve = cooling intensity × min ± S.E.M.). Ethanol is present to faciliate the solubility of the tested agent.
*P < 0.01 t-test.

Many cooling agents are more soluble in ethanol than in 1,2-propanediol. For example, W-3 and CPS-369 are soluble in absolute ethanol at >300 mg/ml and >500 mg/ml, respectively. These compounds are less soluble in 1,2-propanediol, with solubilities of about 10 mg/ml at standard conditions. To formulate liquid compositions of cooling agents, it is convenient to use up to 5% of ethanol in the total volume to dissolve the cooling agent and then add the rest as (R)-1,2-propanediol to complete the formulation without significant loss of cooling actions. Experimentally, it has been found that a solution of (R)-1,2-propanediol containing 1 to 3% ethanol (by volume) does not affect the intensity or duration of cooling, even though in vitro experiments suggest that such low concentrations of ethanol interfere with receptor activation. In the philtrum assay, 100% (R)-1,2-propanediol with 2.5 mg/ml of CPS-369 gave AUC of 107±13 units versus a 106±12 units for a 1% ethanol-99% (R)-1,2-propanediol solvent containing 2.5 mg/ml of CPS-369. Thus, 1% ethanol did not affect cooling action of CPS-369.

For the skin, the 1 to 3% ethanol-97 to 99% (R)-1,2-propanediol solvent containing 2 to 10 mg/ml of CPS-369, CPS-410, and CPS-412 are essentially completed and elegant formulations of a topical medication that can be used to treat irritation, itch or pain. The (R)-1,2-propanediol has the advantage that it does not impart a "greasy" feel to the skin which is obtained with standard topical excipients such as petrolatum and mineral oil, yet the active ingredient is evenly distributed on the skin as a liquid. As shown in further examples, this liquid formulation can be applied directly to the scalp or to the skin.

Ethanol, isopropanol, and racemic 1,2-propanediol are used extensively as solvents for cooling agents. In practice, it may not be economical to completely replace these alcohols with (R)-1,2-propanediol as the primary solvent. For high value products such as pharmaceuticals, eye drops, perfumes or after-shave lotions, however, it may be desirable to optimize the cooling sensation by increasing the fraction of (R)-1,2-propanediol in the liquid composition.

Example 3

(−)-Menthol is the most widely used cooling agent in commercial applications. It is present in a diverse number of liquid or semi-liquid preparations such as in Ben-Gay ointment, IcyHot® medicated patch, and in Vicks Vaposteam Liquid Medication. The effects of (−)-menthol on sensory systems are complex, but one of the target receptors is thought to be the TRP-M8 receptor. The cooling effect of (−)-menthol, 10 mg/ml, in the philtrum assay was compared with either 1,3-propanediol or (R)-1,2-propanediol as the solvent. The results for cooling duration were: 1,3-propanediol 13±1 min and for (R)-1,2-propanediol, 21±2 min, a significant difference (P<0.001). Clearly, (−)-menthol has more cooling activity when dissolved in (R)-1,2-propanediol than in 1,3-propanediol

Example 4

In pharmacology terminology, an antagonist is a chemical that blocks the actions of an agonist, without itself producing an effect. Thus, ethanol, for example, acts as an agonist to inhibit TRP-M8 activation, and an antagonist blocks the ethanol's agonist effect without itself producing any alterations in receptor function. (R)-1,2-propanediol may function as a receptor antagonist at the ethanol (and propanol) binding site of TRP-M8. To test this hypothesis (R)-1,2-propanediol was added at 10%, 20% and 40% volume to volume to an ethanolic solution (100% ethanol) containing 10 mg/ml of WS-5, a known cooling agent. WS-5, 10 mg/ml in 100% ethanol, did not produce any cooling effect when applied to the philtrum. (R)-1,2-propanediol reversed the ethanol inhibition in a dose-dependent relationship. These data, shown in FIG. 2, produced strong evidence that (R)-1,2-propanediol is a specific antagonist at the ethanol/propanol binding site of TRP-M8.

Another cooling agent, WS-3, is widely used is cosmetics, toothpastes and comestibles. WS-3, dissolved 20 mg/ml in absolute ethanol, did not produce significant cooling when it was applied to the philtrum. When WS-3, 20 mg/ml, was dissolved in 97% (R)-1,2-propanediol-3% ethanol, it produced robust cooling lasting 38±3 min, together with prickling and stinging sensations. As shown in Table 2, WS-3 is much less active when dissolved in racemic 1,2-propanediol than in (R)-1,2-propanediol. Thus, the solvent carrier is a critical determinant of biological activity.

Example 5

The cooling properties of certain trialkylphosphine oxides were first described by Rowsell, D. and Spring, D. J. [Phosphine oxides having a physiological cooling effect. U.S. Pat. No. 4,070,496, Jan. 24, 1978]. The general chemical structures of these compounds are shown in Formula 2. A representative prototype is CPS-148 (Formula 2A).

$$R_1R_2R_3P=O \qquad \text{Formula 2}$$

$R_1$ is an alkyl radical containing at least 3 carbon atoms, $R_2$ is an alkyl, cycloalkyl, or alkyl-substituted cycloalkyl radical containing at least 3 carbon atoms, $R_3$ is an alkyl, cycloalkyl, or alkyl-substituted cycloalkyl radical containing at least 3 carbon atoms, $R_1$, $R_2$ and $R_3$ together provide a total of from 13-20 carbon atoms, and At least one of $R_1$, $R_2$ and $R_3$ has branching in an α-, β-, or γ-position relative to the phosphorus atom. Preferably $R_1$, $R_2$ and $R_3$ are such that any two, when taken together, present a total of at least 6 carbon atoms.

Optionally, $R_2$ and $R_3$ may be taken together, with the phosphorus atom, to form a saturated heterocyclic ring of from 5 to 8 atoms, said ring being alkyl-substituted in the 1-position by group $R_1$ and, in addition, also preferentially alkyl-substituted in the 2, or 3 positions.

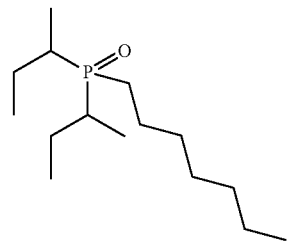 [SMILES: CCCCCCCP(=O)(C(C)CC)C(C)CC]

Formula 2A. Structure of CPS-148: 1-(Di-sec-butyl-phosphinoyl)-heptane, a colorless liquid at STP. Mol. Wt. 260.40. CPS-147 is 1-(Di-sec-butyl-phosphinoyl)-hexane.

CPS-147 and CPS-148 are chemically distinct from the N-alkyl-cycloalkyl-carboxamides which contain 2-isopropyl-5-methyl-cyclohexane. The binding site of the trialkylphosphine oxides on the TRP-M8 receptor is not known. From the data in Table 2, it can be seen that both CPS-147 and CPS-148 are more active when formulated in (R)-1,2-propanediol than in racemic 1,2-propanediol. This is a new and unexpected observation. Trialkylphosphine oxides with cooling properties have applications in the therapy of dermatological conditions such as actinic keratoses, skin cancer, psoriasis, and itch. An ideal solvent delivery vehicle for the trialkylphosphine oxides would be (R)-1,2-propanediol. Trialkylphosphine oxides are soluble in water, but water is not a good vehicle for delivery of pharmaceutical ingredients to the skin because aqueous solutions are not retained on the skin surface.

Example 6

An individual developed intense itch (contact dermatitis) on the scalp at the base of the skull after use of hair dye. A cotton-tipped stick was used to apply CPS-410 or CPS-412, 5 mg/ml dissolved in a 1% ethanol-99% (R)-1,2-propanediol, to the site of itch. The itch sensations were suppressed within 5 min of application of either solution and this effect lasted for at least 8 hr. In a second experiment, the solutions were applied using a plastic bottle with a conical Yorker spout. This allowed more precise droplet delivery of the solution to the site of itch. CPS-410 produced sensations of coolness after application but this was less noticeable with CPS-412. After two days of applications, spaced approximately 10 hours apart, the itch was no longer present. These results were surprising because the scalp is thick relative to the philtrum skin and the receptors for thermosensation are thought to be located at least 1 mm beneath the skin surface, at the junction of the epidermis and subcutaneous tissues. The advantage of liquid formulation is the ease of uniform delivery to the inflamed site, a method not achievable with cream or ointment. Itch symptoms of hair and fur occur in seborrheic dermatitis, psoriasis, insect bites, canine pruritus, and allergic dermatitis. Liquid formulations containing (R)-1,2-propanediol and a cooling agent may be therapeutically valuable in these conditions.

Example 7

A 34-year old male with an 8-year history of plaque psoriasis complained of an axillary skin lesion that itched, had burning sensations, and kept him awake at night. His condition was severe and chronic. His mother complained that she had to vacuum his bedroom every day in order to remove flaking skin debris. Upon examination, the individual had some silvery, flaky lesions on his elbow and knee surfaces, but this did not bother him as much as the skin lesion under his right axilla which was manifested as a rectangular area of about 2×4 cm, with diffuse redness and a moist appearance. He volunteered to try CPS-148, 2% dissolved in 1% ethanol-99% (R)-1,2-propanediol, and was given instructions on how to apply the solution to his site of itch with a swab stick (Q-tip™). He claimed after the first time of application at night the burning sensations and itch disappeared within 5 to 10 min and he was able to have a good night's sleep. He continued to use the solution on an "as-needed basis" for one month and claimed that he slept much better than before. Subsequently, the individual was treated with a course of Enbrel® and his psoriatic condition improved considerably so there was no longer a need for a topical antipruritic drug.

It is to be understood that while the invention has been described above in conjunction with preferred specific embodiments, the description and examples are intended to illustrate and not limit the scope of the invention, which is defined by the scope of the appended claims.

The invention claimed is:
1. An adjuvant useful for topical cooling consisting of:
a cooling agent and a therapeutically effective quantity of (R)-1,2-propanediol in which the cooling agent is dissolved, the quantity of (R)-1,2-propanediol being sufficient to substantially protect the cooling agent's cooling activity from inhibition when in the presence of a short-chain alcohol, and wherein the cooling agent is selected from 1-(Di-sec-butyl-phosphinoyl)-hexane, 1-(Di-sec-butyl-phosphinoyl)-heptane, and mixtures thereof.

* * * * *